United States Patent [19]

Drake

[11] 4,003,933

[45] Jan. 18, 1977

[54] HYDROGENATION OF NITRILES IN ABSENCE OF SECONDARY REACTION SUPPRESSANT

[75] Inventor: Charles A. Drake, Nowata, Okla.

[73] Assignee: Phillips Petroleum Company, Bartlesville, Okla.

[22] Filed: July 16, 1975

[21] Appl. No.: 596,350

[52] U.S. Cl. .......................... 260/583 K; 252/472; 260/570.5 P; 260/578; 260/583 P; 260/584 C; 260/563 C

[51] Int. Cl.² ........................................ C07C 87/14

[58] Field of Search ....... 260/583 K, 583 H, 583 P, 260/570.5 P, 578

[56] References Cited

UNITED STATES PATENTS

| | | | |
|---|---|---|---|
| 3,350,439 | 10/1967 | Feldman et al. | 260/583 K |
| 3,408,397 | 10/1969 | Feldman et al. | 260/583 K |
| 3,898,286 | 8/1975 | Drake | 260/583 P |

FOREIGN PATENTS OR APPLICATIONS

| | | |
|---|---|---|
| 603,825 | 6/1948 | United Kingdom |

OTHER PUBLICATIONS

Freidlin et al. Chem. Abstracts 55(1961) col. 18578a.

Primary Examiner—Arthur P. Demers

[57] ABSTRACT

Nitriles are converted to primary amines in the absence of a secondary amine formation suppressant by hydrogenation of the nitriles in the presence of a catalyst comprising at least one Group VIII metal promoted by at least one Group IVB metal. The process is applicable to the hydrogenation of nitriles having the formula $(A)_xR(C \equiv N)_y$ wherein $x$ is zero or an integer and $y$ is an integer, R is a hydrocarbyl radical having from 2 to 30 carbons and a valence of $x + y$ and each A is selected from the group consisting of —OR' and —NR'$_2$ wherein R' is hydrogen or a hydrocarbyl radical having from 1 to 10 carbon atoms. The process is particularly applicable to the hydrogenation of olefinically unsaturated dinitriles. The complete hydrogenation of olefinically unsaturated nitriles can be carried out in two sequential stages, utilizing a Group IVB metal promoted Group VIII metal catalyst in the first stage to achieve a reduction of the nitrile unsaturation and a suitable catalyst, e.g. ruthenium, in the second stage to achieve a reduction of the olefinic unsaturation.

16 Claims, No Drawings

HYDROGENATION OF NITRILES IN ABSENCE OF SECONDARY REACTION SUPPRESSANT

This invention relates to a process for the preparation of primary amines from nitriles. In one aspect the invention relates to a process for converting olefinically unsaturated aliphatic dinitriles into saturated aliphatic diamines. In another aspect the invention relates to a process for converting nitriles to primary amines in the absence of a secondary amine formation suppressant.

In the hydrogenation of nitriles to primary amines, it is generally deemed desirable to conduct the hydrogenation in the presence of a suppressor for secondary amine formation, e.g. ammonia, tertiary alkyl amines having 3 to 15 carbon atoms, and the like. However, the use of a secondary reaction suppressant increases the cost of chemicals for the process, reduces the throughput of the equipment, and complicates the separation of the reaction effluent. Furthermore in two stage processes for the hydrogenation of olefinically unsaturated nitriles wherein the reduction of the nitrile unsaturation is accomplished in the first stage in the presence of a secondary amine formation suppressant and the olefinic unsaturation is reduced in the second stage, it is generally desirable to separate the suppressant from the first stage reaction effluent before the introduction of the rest of the first stage reaction effluent into the second stage. Thus, it would be advantageous if the nitriles could be converted to primary amines in good yields in the absence of a secondary amine suppressant.

Accordingly, it is an object of the invention to provide a new and improved process for the conversion of nitriles to primary amines. It is an object of the invention to hydrogenate nitriles to produce primary amines in the absence of a secondary amine formation suppressant. It is an object of the invention to eliminate the need for a secondary amine formation suppressant in the hydrogenation of nitriles. Another object of the invention is to simplify the separation of the reaction effluent in a nitrile hydrogenation process. A further object of the invention is to provide an efficient two stage process for the catalytic hydrogenation of a mixture of branched-chain olefinically unsaturated aliphatic dinitriles to produce saturated aliphatic diamines. Still another object is to provide an efficient process for the catalytic hydrogenation of branched-chain unsaturated aliphatic dinitriles under reaction conditions which limit the occurrence of byproduct reactions. Other objects, aspects and advantages of the invention will be apparent from a study of the specification and the appended claims.

The nitriles which can be employed in the present process have the formula $A_xR(C \equiv N)_y$ wherein $x$ is zero or an integer and $y$ is an integer, R is an unsubstituted hydrocarbyl radical having a valence of $x + y$, each A is individually selected from the group consisting of —OR' and —NR'$_2$ radicals wherein each R' is individually selected from the group consisting of hydrogen and unsubstituted hydrocarbyl radicals. While nitriles having any value of $x$ and $y$ can be employed, the value of $x$ will generally be in the range of 0 to 4 and the value of $y$ will generally be in the range of 1 to 4. Similarly, while nitriles having any number of carbon atoms can be employed, in general R will have from 2 to 30 carbon atoms, preferably from 4 to 20 carbon atoms, and each R' will have from 0 to 10 carbon atoms, preferably from 0 to 7 carbon atoms. R can be a saturated acyclic hydrocarbyl radical, a saturated cyclic hydrocarbyl radical, an olefinically unsaturated acyclic hydrocarbyl radical, an olefinically unsaturated cyclic hydrocarbyl radical, or an aromatic radical or any combination thereof. The aromatic radical can have any desired number of rings, but the aromatic radical will generally be monocyclic. Examples of useful nitrile compounds include acetonitrile, caprinitrile, palmitonitrile, cyanocyclohexane, benzonitrile, acrylonitrile, adiponitrile, 1,9-nonanedinitrile, isophthalonitrile, tricyanoethylene, tetracyanoethylene, 1,3,5-tricyanobenzene, 1,2,4,5-tetracyanobenzene, p-aminobenzonitrile, p-(methylamino)benzonitrile, p-(dimethylamino)benzonitrile, hydracrylonitrile, 3-methoxypropionitrile, and mixtures thereof.

The invention is particularly applicable to the two stage hydrogenation of the olefinically unsaturated nitriles of the above formula. In the first stage the olefinically unsaturated nitriles are contacted with hydrogen under suitable hydrogenation reaction conditions in the presence of a catalyst comprising at least one Group VIII metal and at least one Group IVB metal in the absence of any secondary amine formation suppressant, thereby converting the nitriles to primary amines. In the second stage, the reaction effluent from the first stage (or the olefinically unsaturated primary amines separated therefrom, if desired) is contacted with hydrogen under suitable hydrogenation reaction conditions in the presence of a suitable catalyst for the conversion of the olefinically unsaturated amines to saturated amines.

The present process is particularly advantageous for the two stage hydrogenation of olefinically unsaturated dinitriles of the formula:

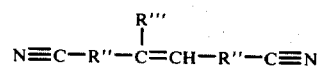

wherein each R" is independently selected from the group consisting of an alkylene radical and an alkylidene radical, and R''' is an alkyl radical. Each R" will generally have from 1 to 15 carbon atoms, preferably from 1 to 6, and more preferably from 1 to 3 carbon atoms. R''' will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms. The branched-chain unsaturated aliphatic dinitriles of formula (I) have been found to be particularly difficult to hydrogenate with many of the conventional hydrogenation catalysts, but can be readily hydrogenated in accordance with the process of the present invention.

Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

If desired, other nitrile reactants can be present and effectively hydrogenated during the hydrogenation of the unsaturated dinitriles of formula (I). Thus, in addition to the unsaturated dinitrile reactants of formula (I), the dinitrile feedstock can contain one or more olefinically unsaturated dinitrile reactants of the formula:

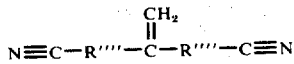
(II)

wherein each R'''' is independently selected from the group consisting of an alkylene radical and an alkylidene radical. In general, each R'''' will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Nitriles having a structure other than that of formulas (I) and (II) can be present during the hydrogenation of these dinitriles, if desired. Similarly, other compounds which may be found in the feed source of the dinitriles of formulas (I) and (II) can be present so long as such additional compounds do not significantly adversely affect the hydrogenation of the dinitriles of formulas (I) and (II). In a presently preferred process for the hydrogenation of dinitriles of formula (I), the dinitriles of formula (I) generally constitute at least 0.1 weight percent, preferably at least 5 weight percent, and more preferably at least 10 weight percent of the total nitriles in the feedstock.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

In the practice of this invention, the catalytic hydrogenation of the nitriles having the formula $(A)_xR(C \equiv N)_y$ results primarily in the formation of primary amines having the formula $(A)_xR(C-H_2-NH_2)_y$, wherein A, R, $x$ and $y$ are as defined hereinabove. Similarly, the catalytic hydrogenation of the unsaturated dinitrile reactant of formula (I) results primarily in the formation of saturated diamine reaction products having the formula:

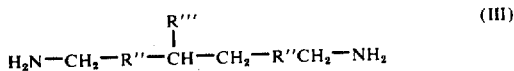
(III)

wherein R'' and R''' are as defined hereinbefore. The catalytic hydrogenation of an unsaturated dinitrile reactant of formula (II) results primarily in the formation of saturated diamine reaction products having the formula:

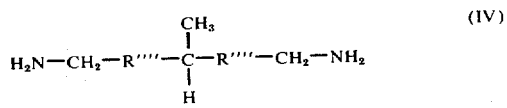
(IV)

wherein R'''' is as defined hereinbefore.

The practice of this invention is particularly suited to the catalytic hydrogenation of olefinically unsaturated nitriles, e.g. a mixture of species of formula (I) and formula (II), for the purpose of achieving saturated amine reaction products which are substantially free of any olefinic unsaturation. The phrase "substantially free of olefinic unsaturation" signifies that the amine reaction products contain less than about 1 weight percent olefinically unsaturated amine reaction product based on the total weight of unsaturated and saturated amine reaction products wherein the weight percents are determined by conventional methods such as by gas-liquid chromatographic analysis (GLC). The phrase "essentially free of olefinic unsaturation" signifies that the amine reaction products contain less than about 0.1 weight percent olefinically unsaturated amine reaction product based on the total weight of unsaturated and saturated amine reaction products wherein the weight percents are determined by conventional methods such as by GLC analysis techniques. The diamine reaction products composed primarily of diamines having formula III or IV, and which are at least substantially free, and preferably essentially free, of olefinic unsaturation are advantageously employed in the preparation of linear terephthalamide polymers.

One of the most important advantages of the catalytic hydrogenation process of this invention is directly related to the production of a mixture of diamines which are essentially free of olefinic unsaturation from the unsaturated dinitrile product mixture produced by the reaction of acrylonitrile and isobutylene. This advantage is significant since early prior art processes for the catalytic hydrogenation of the acrylonitrile and isobutylene reaction product mixture failed to substantially or completely reduce the olefinic unsaturation of the unsaturated dinitrile feedstock, thereby producing a reaction product mixture containing branched-chain aliphatic diamines having substantial olefinic unsaturation in the carbon skeleton. The separation of the branched-chain olefinically unsaturated diamines from the saturated diamines is inconvenient, and polyamides prepared from the mixtures containing a significant amount of unsaturated diamines have been found to be unsuited or undesirable in the preparation of polyamide fibers, particularly the terephthalamide polymers.

Thus, the catalytic hydrogenation of this invention is advantageous in the preparation of such polyamides.

The catalysts that are considered to be suitable for employment in the single stage hydrogenation of saturated nitriles and in the first stage of the two stage hydrogenation of olefinically unsaturated nitriles include a first component and a second component. The first component is selected from the group consisting of elemental Group VIII metals and compounds of elemental Group VIII metals which are reducible by hydrogen to the corresponding finely divided elemental metal at the hydrogenation conditions employed in the single stage or the first stage, and mixtures thereof. The second component is selected from the group consisting of elemental Group IVB metals and compounds of elemental Group IVB metals which are reducible by hydrogen to the corresponding finely divided elemental metal at the hydrogenation conditions employed in the single stage or the first stage, and mixtures thereof. Suitable reducible compounds include the oxides, halides, nitrates, sulfates, oxalates, acetates, carbamates, propionates, tartrates, hydroxides, and the like, and mixtures thereof. Specific examples of the first component include elemental iron particles, ferrous oxide, ferrous chloride, ferric acetate, elemental ruthenium particles, ruthenium oxide, ruthenium chloride, ruthenium nitrate, ruthenium acetate, elemental osmium particles, osmium oxide, osmium chloride, Raney cobalt, elemental cobalt particles, cobalt chloride, cobalt nitrate, cobalt acetate, cobalt hydroxide, elemental rhodium particles, rhodium oxide, rhodium chloride, rhodium acetate, rhodium carbonate, elemental iridium particles, iridium oxide, iridium chloride, elemental nickel particles, Raney nickel, nickel oxide, nickel chloride, nickel nitrate, nickel oxalate, nickel hydroxide, elemental palladium particles, palladium oxide, palladium chloride, palladium acetate, elemental platinum particles, platinum oxide, platinum chloride, platinum acetate, and the like, and mixtures thereof. Cobalt and its compounds as stated above are preferred. Specific examples of the second component include elemental titanium particles, titanium oxide, titanium chloride, titanium acetate, titanium oxalate, elemental zirconium particles, zirconium oxide, zirconium chloride, zirconium hydroxide, elemental hafnium particles, hafnium oxide, hafnium chloride, hafnium acetate, and the like, and mixtures thereof. Zirconium and its compounds as stated above are preferred.

The weight ratio of said second component to said first component can be any value at which the combination is effective to enable the conversion of the nitrile to a primary amine in the absence of a secondary amine formation suppressant. In general, the weight ratio of the second component to the first component, based on elemental metal, will be in the range of about 0.001:1 to about 0.2:1, preferably in the range of about 0.005:1 to about 0.1:1, and more preferably in the range of about 0.01:1 to about 0.05:1. The first stage catalyst can be unsupported, but generally will be employed on a solid support. Suitable supports include kieselguhr, charcoal, alumina, silica, calcium carbonate, barium carbonate, asbestos, pumice, clays, and the like, and mixtures thereof. In a supported catalyst, the total content of the first and second components, calculated as elemental metal, will generally constitute from about 1 to about 90 weight percent of the total first step catalyst composition and preferably will be in the range of about 40 to about 70 weight percent of the total first stage catalyst composition.

The first stage catalyst can be prepared by any suitable method known in the catalyst preparation art. The Group VIII, Group IVB and support components can be associated using any suitable techniques such as impregnation, coprecipitation, and the like together with suitable methods for calcination, reduction to the metal, tableting, etc. Depending upon the mode of reaction desired, the supported catalyst can be in the form of powder, agglomerates, granules, tablets, pills, or the like.

The weight ratio of first stage catalyst to the nitrile reactants can be varied as desired. For purposes of maintaining reasonable reaction rates under economically attractive catalyst reaction kinetics, it is generally preferred that the weight ratio of the total of the Group VIII metal and the Group IVB metal, calculated as elemental metal, to the nitrile reactants be in the range of about 0.01:100 to about 30:100, preferably in the range of about 0.1:100 to about 20:100, and more preferably in the range of about 5:100 to about 15:100.

The catalysts that are considered to be suitable for employment in the second stage of the two stage process for the catalytic hydrogenation of olefinically unsaturated amines in accordance with this invention include at least one member selected from the group consisting of finely divided elemental cobalt, finely divided elemental rhodium, finely divided elemental palladium, finely divided elemental ruthenium, elemental nickel, compounds of cobalt, nickel, ruthenium, rhodium or palladium which are reducible by hydrogen to the corresponding finely divided elemental metal, and mixtures thereof. Suitable reducible compounds include the oxides, halides, nitrates, sulfates, oxalates, acetates, carbamates, propionates, tartrates, hydroxides, and the like, and mixtures thereof. Specific examples of reducible compounds include Raney cobalt, cobalt oxide, cobalt chloride, cobalt acetate, cobalt carbonate, cobalt hydroxide, ruthenium oxide, ruthenium chloride, ruthenium nitrate, ruthenium acetate, ruthenium carbonate, ruthenium hydroxide, Raney nickel, nickel oxide, nickel chloride, nickel nitrate, nickel oxalate, nickel acetate, nickel hydroxide, rhodium oxide, rhodium chloride, rhodium nitrate, rhodium acetate, palladium oxide, palladium chloride, palladium acetate, palladium hydroxide, and the like, and mixtures thereof. The weight ratio of the second stage catalyst to unsaturated amine reactant can be varied as desired. For the purpose of maintaining reasonable reaction rates under economically attractive catalyst reaction kinetics, it is generally preferred that the weight ratio of the total of cobalt nickel, ruthenium, rhodium, and palladium, calculated as elemental metal, to the unsaturated amine reactants be maintained within a range of about 0.01:100 to about 30:100, and preferably in the range of about 0.1:100 to about 20:100, and more preferably in the range of about 1:100 to about 15:100.

It is often desirable to employ catalytic amounts of the second stage catalyst components supported by a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures thereof. The cobalt, nickel, ruthenium, rhodium and/or palladium catalyst can be added to the catalyst support by any of the methods well known in the art. For example, the support catalysts can be prepared by dry mixing the components or by impregnating the support with a solution or dispersion of cobalt, nickel, ruthenium, rhodium and/or palladium in elemental form or in the form of reducible compounds thereof. The supported catalyst can be pretreated with hydrogen to reduce the compounds, or such reduction can be achieved in the second stage hydrogenation reactor at the hydrogenation conditions employed therein. When a support is employed, the elemental cobalt, nickel, ruthenium, rhodium and/or palladium content will generally be in the range of about 0.1 to about 50 weight percent, preferably in the range of about 0.2 to about 10 weight percent, based on the weight of the total catalyst components. Presently preferred catalysts include ruthenium or alumina having a ruthenium metal content of about 0.5 percent by weight, based on the total weight of the catalyst and the support material, and Raney nickel. These presently preferred catalytic forms, as well as other suitable catalysts such as 5 weight percent ruthenium on charcoal, are commercially available.

Any catalytic hydrogenation temperature can be employed which provides the desired degree of catalytic efficiency in the hydrogenation of the nitrile containing feedstock. The hydrogenation temperature in a single stage and in the first stage of a two stage process will generally be within the range of about 30° C to about 300° C., and preferably will be within the range of about 70° C to about 150° C. The hydrogenation temperature in the second stage of a two stage process will generally be within the range of about 100° C to about 250° C and preferably will be within the range of about 120° C to about 200° C.

The catalytic hydrogenation of nitriles can be carried out in a single stage process or in the first stage of a two stage process at any hydrogen pressure wherein the nitrile groups are reduced in the presence of hydrogen and in the absence of a secondary amine formation suppressant. The catalytic hydrogenation of the olefinic unsaturation can be carried out in the second stage of a two stage process at any suitable hydrogenation pressure. Generally, suitable hydrogen pressures for a single stage process and for each stage of a two stage process are within the range of from about 500 to about 5000 psig, but lower or even higher hydrogen pressures can be employed. Preferably, due to economic considerations, hydrogen pressures within the range of about 1000 to about 3000 psig are employed. It may be desirable to employ higher hydrogen pressures at lower reaction temperatures to achieve the desired degree of hydrogenation within a reasonable amount of time.

Any contact time interval suited for the desired catalytic hydrogenation in a single stage or in each stage of a two stage process can be employed in the practice of this invention. However, time intervals economically attractive to the process are generally within the range of about 15 minutes to about 5 hours for a single stage process or for the first stage of a two stage batch hydrogenation process, and generally within the range of about 15 minutes to about 5 hours for the second stage of the batch process. A total reaction time in the range of about 1 to about 6 hours for a two stage process is presently preferred in order to insure substantially complete hydrogenation of any olefinically unsaturated bonds in the feedstock as well as complete hydrogenation of the nitrile groups to primary amino groups. The catalytic hydrogenation of nitriles in accordance with the process of this invention can be carried out as a continuous process at any suitable liquid hourly space velocity (LHSV). However, the liquid hourly space velocity rates will generally be within the range of about 0.1 to about 10, preferably in the range of about 0.2 to about 5, and more preferably in the range of about 0.5 to about 2, volumes of nitrile reactant plus diluent per volume of catalyst (including the volume of any catalyst support if any is present) per hour.

It is desirable that each stage of the hydrogenation reaction be carried out in the presence of a suitable diluent. While any suitable diluent can be employed in any stage, it is preferable that the diluent be selected from the class consisting of unsubstituted alkanols containing from 1 to 12 carbon atoms per molecule, unsubstituted acyclic and unsubstituted cyclic ethers having 4 to 2 carbon atoms per molecule, saturated hydrocarbons having 4 to 12 carbon atoms per molecule, and mixtures thereof. The term "unsubstituted" indicates that there are no substituents other than hydrocarbyl radicals. Examples of alkanol diluents include methanol, ethanol, 2-propanol, 2-methyl-2-propanol, 2-methyl-2-butanol, 2-ethyl-2-hexanol, 2-butanol, 1-hexanol, 1-octanol, 2-decanol, 1-dodecanol, and the like, and mixtures thereof. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include diethyl ether, 1,3-dioxane, 1,4-dioxane, tetrahydrofuran, 4,4-dimethyl-1,3-dioxane, and mixtures thereof. To facilitate handling of the reaction mixtures, the weight ratio of nitrile or amine reactants to diluent charged to the particular reaction zone is generally within the range of about 0.001:100 to about 20:100, and is preferably in the range of about 0.1:100 to about 15:100.

The first stage of the present invention provides for essentially complete hydrogenation of the nitrile functions of formulas (I) and (II) without requiring the presence of ammonia or amines to suppress the formation of secondary amines or heavies. Some of the olefinic unsaturation of the feed, particularly the more easily reduced olefinic unsaturation of formula (II), can also be hydrogenated in the first stage. The second stage of the hydrogenation process provides essentially complete hydrogenation of the olefinic unsaturation remaining from the first step, particularly the more difficultly reducible olefinic unsaturation of formula (I).

At the conclusion of a single stage reaction process, the reaction effluent can be processed through conventional separation means to recover the diluent and/or catalyst and to separate the desired amine product, any byproducts and any unreacted nitriles. In a two stage process wherein the diluent is the same in both stages, the reaction effluent from the first stage can be passed directly to the second stage or it can be treated to remove the catalyst and/or byproducts before introduction into the second stage. It is also within the scope of this invention to recover the product from the first reaction stage by separation of the same from the catalyst, diluent, and byproducts, and to utilize this product along with fresh catalyst and diluent as the charge to the second stage reaction.

Processing of the effluent from the second stage reaction of a two step process for the recovery of the desired end product, as well as any resulting reaction byproducts, any unconsumed reactants, hydrogen, and/or diluents can be carried out by any conventional separation means. In general, at the conclusion of the second stage of the catalytic hydrogenation process, the reaction effluent is cooled and depressurized with the recovery, if desired, of any diluent which is vented from the reaction effluent during the depressurization operation. The diluent can be returned or recycled to either reaction stage if desired. The reaction products can be separated from the catalyst by conventional filtration means. The filtrate containing the at least substantially completely saturated amines can be conveniently separated from any reaction byproducts or any diluent remaining in the filtrate by any conventional fractional distillation.

The following examples are presented in further illustration of the invention.

EXAMPLE I

The following run in accordance with the invention illustrates the use of a two stage hydrogenation of a mixture of olefinically unsaturated dinitriles consisting of approximately 52 weight percent 5-methylenenonanedinitrile, approximately 25 weight percent 5-methyl-4-nonenedinitrile, approximately 12 weight percent of the combination of 2,4-dimethyl-4-octenedinitrile, 2-methyl-4-methyleneoctanedinitrile, and 2,4-dimethyl-3-octenedinitrile, and approximately 1 weight percent of the combination of 2,6-dimethyl-4-methyleneheptanedinitrile and 2,4,6-trimethyl-3-heptenedinitrile.

FIRST STAGE REACTION

A 10 percent by weight solution of the above described dinitrile mixture in 2-methyl-2-propanol was pumped continuously at a rate of approximately 1 ml/min through a 60 ml reactor packed with an 8–12 mesh catalyst consisting of 60 weight percent cobalt, 2.2±0.2 weight percent zirconium, and a kieselguhr support, each of these percentages being based on the total catalyst composition. The reactor was maintained at 120° C and 1500 psig hydrogen pressure and free of any secondary amine formation suppressant. A total of 450 ml of reaction effluent mixture was collected over an 8 hour interval during which 38.4 gm of said dinitrile mixture was introduced into said reactor. A sample of the collected reactor-effluent mixture was analyzed by gas-liquid chromatograph (glc). The analysis showed complete nitrile reduction and 35.7 gm of primary diamines (88 percent of theoretical yield) of which approximately 50 weight percent was unsaturated and 4.8 gm of heavies including any secondary diamines.

SECOND STAGE REACTION

The reaction effluent mixture from the first stage was pumped continuously at a rate of approximately 1 ml/min through a 60 ml reactor packed with 0.5 weight percent ruthenium on high purity alumina (1/32 inch granules prepared from aluminum alkoxides). The reactor was maintained at 130° C and 1500 psig hydrogen pressure. A total of 365 ml of reaction effluent mixture, which collected over a 6.5 hour interval, was concentrated using a rotary evaporator to give 38 gm of liquid. A glc analysis of the concentrated liquid showed complete olefinic reduction and 28.5 gm of saturated aliphatic primary diamines (80.7 percent of theoretical yield) and 9.5 gm of heavies including any secondary diamines.

COMPARATIVE EXAMPLE A

The following comparative run shows the first stage hydrogenation of the dinitrile mixture described in Example I using unpromoted cobalt as the catalyst.

A 10 percent by weight solution of the dinitrile mixture described in Example I in 2-methyl-2-propanol was pumped continuously at a rate of approximately 1 ml/min through a 60 ml reactor packed with an 8–12 mesh catalyst consisting of 60 weight percent cobalt and 40 weight percent kieselguhr support, the percentages being based on total catalyst composition. The reactor was maintained at 120° C and 1500 psig hydrogen pressure and free of any secondary amine suppressant. A total of 485 ml of reaction effluent mixture was collected over an 8 hour interval, during which 38.8 gm of said dinitrile mixture was charged to said reactor. The collected reaction effluent was concentrated using a rotary evaporator to remove diluent and then distilled to give 22.1 gm (54 percent of theoretical yield) of primary diamines and 18 gm of heavies including any secondary diamines.

Comparison of the results of this run with the results of the first stage reaction of the run of Example I shows that considerably higher yield of primary diamines was obtained using the process of the present invention. The production of the large amount of heavies observed in the run of Comparative Example A was reduced appreciably in the first stage of the run of Example I by the use of the zirconium-promoted cobalt catalyst.

COMPARATIVE EXAMPLE B

The following comparative run illustrates the use of ammonia in the first stage hydrogenation of the dinitrile mixture described in Example I.

A feed mixture was formed by combined 40 gm of the dinitrile mixture described in Example I, 355 gm of 2-methyl-2-propanol and 80 gm of ammonia. This feed mixture was pumped continuously at a rate of approximately 1 ml/min through a 60 ml reactor packed with an 8–12 mesh catalyst consisting of 60 weight percent cobalt, 2.2±0.2 weight percent zirconium, and a kieselguhr support, each of these percentages being based on the total catalyst composition. The reactor was maintained at 120° C and 1500 psig hydrogen pressure. Reaction effluent mixture was collected over a 6-hour interval and concentrated using a rotary evaporator to 31 gm liquid product. A sample of the concentrated reaction effluent was analyzed by glc and the analysis showed complete nitrile reduction and 27.0 gm of primary diamines (87.1 percent of theoretical yield) and 4 gm of heavies including any secondary amines. A comparison of this run with the first stage reaction of Example I demonstrates that the presence of ammonia is not required during the reduction of the nitrile unsaturation when employing a zirconium promoted cobalt catalyst. Thus excessive side-reactions were avoided using the inventive process, even though it was previously thought that the ammonia or amines were needed to suppress side-reactions.

COMPARATIVE EXAMPLE C

The following comparative run illustrates the use of ruthenium in the absence of ammonia in the first stage hydrogenation of the dinitrile mixture described in Example I.

A 10 percent by weight of the dinitrile mixture described in Example I in 2-methyl-2-propanol was pumped continuously at a rate of approximately 1 ml/min through a 60 ml reactor packed with 60 grams of 1/16 inch particles of 0.5 weight percent ruthenium on high purity alumina. The reactor was maintained at 130° C and 1500 psig hydrogen pressure and free of any secondary amine suppressant. A total of 365 gm of reactor effluent was collected over an 8-hour interval, during which 38.4 gm of said dinitrile mixture was introduced into said reactor. The collected effluent was concentrated by rotary evaporator to give 41.5 gm of concentrate. This concentrate was distilled (120° C at 25 mm) to give 18.6 gm of primary diamines (45.5 percent of theoretical yield) and 22.4 gm heavies including any secondary diamines. This run demonstrates that the use of ruthenium in the first stage hydrogenation in the absence of ammonia is not satisfactory.

Reasonable variations and modifications are possible within the scope of the foregoing disclosure and the appended claims to the invention.

That which is claimed is:

1. A process for the catalytic hydrogenation of at least one nitrile having the formula $(A)_xR(C \equiv N)_y$ wherein $x$ is zero or an integer and $y$ is an integer, R is a hydrocarbyl radical having a valence of $x+y$, and each A is selected from the group consisting of —OR' and —NR'$_2$ wherein each R' is individually selected from the group consisting of hydrogen and hydrocarbyl radicals having from 1 to 10 carbon atoms, to produce primary amines; comprising contacting said at least one nitrile with hydrogen and a catalyst under first suitable hydrogenation conditions in the at least substantial absence of any secondary amine formation suppressant; said catalyst comprising at least one first component selected from the group consisting of elemental Group VIII metals and compounds of Group VIII metals which are reducible by hydrogen to the corresponding elemental metal at said hydrogenation conditions, and at least one second component selected from the group consisting of elemental Group IVB metals and compounds of Group IVB metals which are reducible by hydrogen to the corresponding elemental metal at said hydrogenation conditions.

2. A process in accordance with claim 1 wherein $x$ is zero or an integer in the range of 1 to 4, $y$ is an integer in the range of 1 to 4, and R contains from 2 to 30 carbon atoms.

3. A process in accordance with claim 2 further comprising recovering at least a portion of the primary amines thus produced.

4. A process in accordance with claim 2 wherein the weight ratio of said at least one second component to said at least one first component is in the range of about 0.001:1 to about 0.2:1.

5. A process in accordance with claim 4 wherein said first component is elemental cobalt particles or a compound of cobalt which is reducible by hydrogen to finely divided particles of elemental cobalt at said hydrogenation conditions.

6. A process in accordance with claim 5 wherein said second component is elemental zirconium or a compound of zirconium which is reducible by hydrogen to finely divided particles of elemental zirconium at said hydrogenation conditions.

7. A process in accordance with claim 6 wherein the weight ratio of said elemental zirconium to said elemental cobalt is in the range of about 0.005:1 to about 0.1:1.

8. A process in accordance with claim 7 wherein said at least one nitrile comprises at least one olefinically unsaturated dinitrile of the formula

wherein such R'' has from 1 to 15 carbon atoms and is individually selected from the group consisting of an alkylene radical and an alkylidene radical, and R''' is an alkyl radical having from 1 to 15 carbon atoms.

9. A process in accordance with claim 8 wherein each R'' has from 1 to 6 carbon atoms, and wherein R''' has from 1 to 3 carbon atoms.

10. A process in accordance with claim 9 further comprising recovering at least a portion of the resulting olefinically unsaturated primary diamines and contacting the thus recovered unsaturated primary diamines with hydrogen and a second catalyst under second suitable hydrogenation conditions to produce a primary diamine product at least substantially free of olefinic unsaturation, said second catalyst comprising particles of at least one member of the group consisting of elemental cobalt, elemental nickel, elemental ruthenium, elemental rhodium, elemental palladium and compounds of cobalt, nickel, ruthenium, rhodium or palladium which are reducible by hydrogen to the corresponding elemental metal at said second suitble hydrogenation conditions.

11. A process in accordance with claim 10 wherein said first suitable hydrogenation conditions comprise a temperature in the range of about 30° to about 300° C and a hydrogen pressure in the range of about 500 to about 5000 psig, and wherein said second suitable reaction conditions comprise a temperature in the range of about 100° to about 250° C and a hydrogen pressure in the range of about 500 to about 5000 psig.

12. A process in accordance with claim 11 wherein each of said first and second reaction conditions further comprise the presence of a diluent selected from the group consisting of unsubstituted alkanols having from 1 to 12 carbon atoms per molecule, saturated hydrocarbons having from 4 to 12 carbon atoms per molecule, and unsubstituted ethers having from 4 to 12 carbon atoms.

13. A process in accordance with claim 2 wherein said first component is elemental cobalt particles or a compound of cobalt which is reducible by hydrogen to finely divided particles of elemental cobalt at said hydrogenation conditions.

14. A process in accordance with claim 13 wherein said second component is elemental zirconium or a compound of zirconium which is reducible by hydrogen to finely divided particles of elemental zirconium at said hydrogenation conditions.

15. A process in accordance with claim 2 wherein said second component is elemental zirconium or a compound of zirconium which is reducible by hydrogen to finely divided particles of elemental zirconium at said hydrogenation conditions.

16. A process in accordance with claim 2 wherein said at least one nitrile comprises at least one olefinically unsaturated nitrile, further comprising recovering at least a portion of the resulting olefinically unsaturated primary amine and contacting the thus recovered olefinically unsaturated primay amine with hydrogen and a suitable catalyst under suitable hydrogenation conditions to convert the thus contacted olefinically unsaturated primary amine to a primary amine at least substantially free of olefinic unsaturation.

* * * * *